(12) United States Patent
Oliner et al.

(10) Patent No.: US 6,746,844 B2
(45) Date of Patent: *Jun. 8, 2004

(54) DETERMINING SIGNAL TRANSDUCTION PATHWAYS

(75) Inventors: Jonathan D. Oliner, Newbury, CA (US); Earl Hubbell, Los Angeles, CA (US)

(73) Assignee: Affymetrix, Inc., Santa Clara, CA (US)

( * ) Notice: Subject to any disclaimer, the term of this patent is extended or adjusted under 35 U.S.C. 154(b) by 90 days.

This patent is subject to a terminal disclaimer.

(21) Appl. No.: 10/051,020

(22) Filed: Jan. 22, 2002

(65) Prior Publication Data

US 2002/0094518 A1 Jul. 18, 2002

Related U.S. Application Data

(63) Continuation of application No. 09/431,964, filed on Nov. 1, 1999, now Pat. No. 6,340,565.
(60) Provisional application No. 60/106,912, filed on Nov. 3, 1998.

(51) Int. Cl.⁷ .............................. C12Q 1/68; C12P 21/06
(52) U.S. Cl. .................. 435/6; 4/69.1; 4/91.1; 4/325; 4/375; 4/320.1; 4/91.31; 536/23.1; 536/23.2; 536/24.5
(58) Field of Search ........................... 435/6, 91.1, 325

(56) References Cited

U.S. PATENT DOCUMENTS 5,700,637 A    12/1997  Southern
5,965,352 A *  10/1999  Stoughton et al. ............. 435/4
6,340,565 B1 * 1/2002  Oliner et al. .................. 435/6

FOREIGN PATENT DOCUMENTS

WO    WIPO 89/10977    11/1989

OTHER PUBLICATIONS

Baker et al. "Transducers of Life and Death: INF Receptor Superfamily and Associated Proteins", *Oncooene* 1996, vol. 12, pp. 1–9.
Chinnalyan et al. "Fadd/Mort1 is a Common Mediator of CD95 (fas/APO–1) and Tumor Nacroais Factor Receptor–induced Apoptosis", *Journal of Biological Chemistry*, Mar. 1, 1996, vol. 271, No. 9, pp. 4961–4965.
Akudau et al., "Identification of Gene Regulatory Networks by Strategic Gene Disruptors and Gene Overexpressions", *Procedures of the Ninth ACM–SIAM Symposium on Discrete Algorithams*, (1996), pp. 695–702.
I. Barnard Weinstein, "Strategies for Inhibiting Multistage Carcinogenesis Based on Signal Transduction Pathways", *Mutation Research*, 2002 (1988), pp. 413–420.

* cited by examiner

*Primary Examiner*—Sean McGarry
*Assistant Examiner*—Janet L. Epps-Ford
(74) *Attorney, Agent, or Firm*—Banner & Witcoff, Ltd.

(57) ABSTRACT

Experimental and analytical methods enable reconstruction of signal transduction networks from gene expression profiles. Signal transduction pathways can be reverse-engineered by 1) experimentally manipulating individual genes, 2) generating cellular expression profiles, and 3) analyzing for common patterns among these profiles. Analysis of patterns among profiles permits reconstruction of pathways and networks of interrelationships among genes and their products.

33 Claims, 3 Drawing Sheets

| a. True Graph G | b. Connectivity Data for G |
|---|---|
|  | |

| | | Expressed Genes | | | | |
|---|---|---|---|---|---|---|
| | | A | B | C | D | E |
| Induced Gene | A | 1 | 1 | 1 | 1 | 1 |
| | B | 0 | 1 | 1 | 1 | 1 |
| | C | 0 | 1 | 1 | 1 | 1 |
| | D | 0 | 1 | 1 | 1 | 1 |
| | E | 0 | 0 | 0 | 0 | 1 |

| c. Transitive Closure G* | d. A Graph compatible with Data |
|---|---|
|  |  |

| e. A Graph compatible with Data | f. G* reduced to condensed graph |
|---|---|
|  |  |

Solid arrows are required by the data. Dashed arrows cannot be excluded by the data.

a. True Graph G,
B regulated by A not by expression.

b. Connectivity Data for G

| | Expressed Genes | | | | |
|---|---|---|---|---|---|
| | A | B | C | D | E |
| Induced Gene A | 1 | 0 | 1 | 1 | 0 |
| B | 0 | 1 | 1 | 1 | 0 |
| C | 0 | 0 | 1 | 0 | 0 |
| D | 0 | 0 | 0 | 1 | 0 |
| E | 0 | 0 | 1 | 1 | 1 | c. Transitive Closure G*

DETERMINING SIGNAL TRANSDUCTION PATHWAYS

This is a Continuation Application of parent application Ser. No. 09/431,964, filed Nov. 1, 1999, now U.S. Pat. No. 6,340,565 which claimed the benefit of provisional application Serial No. 60/106,912 filed Nov. 3, 1998, which is expressly incorporated by reference in its entirety herein.

TECHNICAL FIELD OF THE INVENTION

This invention is related functional mediators of genes and functional organization of such mediators into pathways.

BACKGROUND OF THE INVENTION

Many biological functions are accomplished by altering the expression of various genes through transcriptional (e.g. through control of initiation, provision of RNA precursors, RNA processing, etc.) and/or translational control. For example, fundamental biological processes such as cell cycle regulation, cell differentiation and cell death, are often characterized by the variations in the expression levels of groups of genes.

Gene expression is also associated with pathogenesis. For example, the lack of sufficient expression of functional tumor suppressor genes and/or the over expression of oncogene/protooncogenes could lead to tumorgenesis (Marshall, *Cell*, 64: 313–326 (1991); Weinberg, *Science*, 254: 1138–1146 (1991), incorporated herein by reference for all purposes). Thus, changes in the expression levels of particular genes (e.g. oncogenes or tumor suppressors) serve as signposts for the presence and progression of various diseases.

The study of gene expression in the art has been generally concentrated on the regulatory regions of the gene of interest and on the relationships among a few genes. A number of transcriptional factors/DNA binding proteins have been identified and a limited number of regulatory pathways have been discovered. However, the expression of a particular gene is frequently regulated by the expression of a large number of other genes. The expression of those regulatory genes may also be under the control of additional genes. This complex regulatory relationship among genes constitutes a genetic network. The function and regulation of a particular gene can be best understood in the context of this genetic network. As the Human Genome Project and commercial genome research progress at a great rate, most, if not all, of the expressed genes will be partially sequenced in the near future. Understanding the functions and regulatory relationships among the large number of genes is becoming a difficult task with traditional tools.

Communication through signal transduction pathways is usually achieved through a combination of transcriptional and post-transcriptional mechanisms. Because signaling events are causally linked within given pathways, genetic alterations that disrupt either of these two classes of regulatory mechanisms should ultimately affect gene expression.

There is a need in the art to develop a systematic approach to understand the complex regulatory relationships among large numbers of genes, in particular those involved in signal transduction.

SUMMARY OF THE INVENTION

It is an object of the present invention to provide methods of determining candidate functional mediators of genes.

It is another object of the present invention to provide methods for determining a pathway of gene products.

These and other objects of the invention are achieved by providing one or more of the embodiments described below. In one embodiment a method is provided for determining candidate functional mediators of a transgene. The method comprises: altering expression of a first selected gene in a first of two populations of identical cells. Expression levels of a set of genes in the two populations of cells are compared. Genes in the set whose expression levels differ between the two populations of cells are identified. The genes identified are candidate functional mediators of the selected gene. Expression of a second selected gene is then altered in one of a third and fourth populations of cells. The third and fourth populations comprise identical cells. The second selected gene is a candidate functional mediator of the first selected gene. Expression levels of a set of genes in the third and fourth populations of cells are compared. Genes in the set whose expression levels differ between the third and fourth populations of cells are identified. The genes identified are candidate functional mediators of the second selected gene.

According to another embodiment a method is provided for identifying pathways of functional mediators of a selected gene. The method comprises altering expression of a first selected gene in a first of two populations of identical cells. Expression levels of a set of genes in the two populations of cells are compared. Genes in the set whose expression levels differ between the two populations of cells are identified. The genes identified form a set of candidate functional mediators of the first selected gene. Expression of a second selected gene is altered in one of a third and fourth populations of cells which populations comprise identical cells. Expression levels of the set of genes in the third and fourth populations of cells are compared. Genes in the set whose expression levels differ between the third and fourth populations of cells are identified. The genes identified form a set of candidate functional mediators of the second selected gene. The candidate functional mediators identified of the first and second selected genes are compared. Genes which are identified as candidate functional mediators of both selected genes suggest that the first and second selected genes are components of a common pathway. Failure to identify a candidate functional mediator of both selected genes suggests that the two selected genes are in different pathways. Identification of the set of candidate functional mediators of the first selected gene as a subset of the set of candidate functional mediators of the second selected gene suggests that the first selected gene is downstream in a pathway relative to the second selected gene. A candidate functional mediator which is identified in only one of the two sets of candidate functional mediators is identified as upstream in the pathway of a selected gene from a point of convergence with the pathway of the other selected gene, if the sets of candidate functional mediator genes of the first and second selected genes contain common members.

In still another aspect of the invention, a method is provided to determine a pathway of gene products. The method comprises comparing a first set of genes with a second set of genes. The first set is identified by comparing a first set of candidate functional mediator genes with a second set of candidate functional mediator genes. The first set is identified by the process of:

(a) comparing expression levels of a set of genes in two populations of identical cells, wherein a first of the two populations of cells has been treated to alter expression of a first selected gene;

(b) identifying genes in the set whose expression levels differ between the two populations of cells, wherein the genes identified are candidate functional mediators of the first selected gene.

The second set is identified by the process of:

(c) comparing expression levels of the set of genes in a third and fourth population of cells, wherein the third population of cells has been treated to alter expression of a second selected gene;

(d) identifying genes whose expression levels differ between the third and fourth populations of identical cells, wherein the genes identified are candidate functional mediators of the second selected gene.

The first and second selected genes are identified as components of a common pathway when one or more genes are found to be candidate functional mediators of both of said first and said second selected genes. Alternatively, the first and second selected genes are identified as being in different pathways when no gene is identified as being a candidate functional mediator of both of said first and said second selected genes. In another embodiment a gene which is found to be a candidate functional mediator of only one of said first and said second selected genes is identified as upstream in the pathway of the first or second selected gene from a point of convergence with the pathway of the second or first selected gene, if the first and second sets of candidate functional mediator genes contain common members. In still another embodiment the first selected gene is identified as downstream in a pathway relative to the second selected gene if the set of candidate functional mediators of the first selected gene is a subset of the set of candidate functional mediators of the second selected gene.

These approaches can be used to interrogate the genetic regulatory network and to construct a map indicating regulatory relationships.

DETAILED DESCRIPTION

Figure 1:
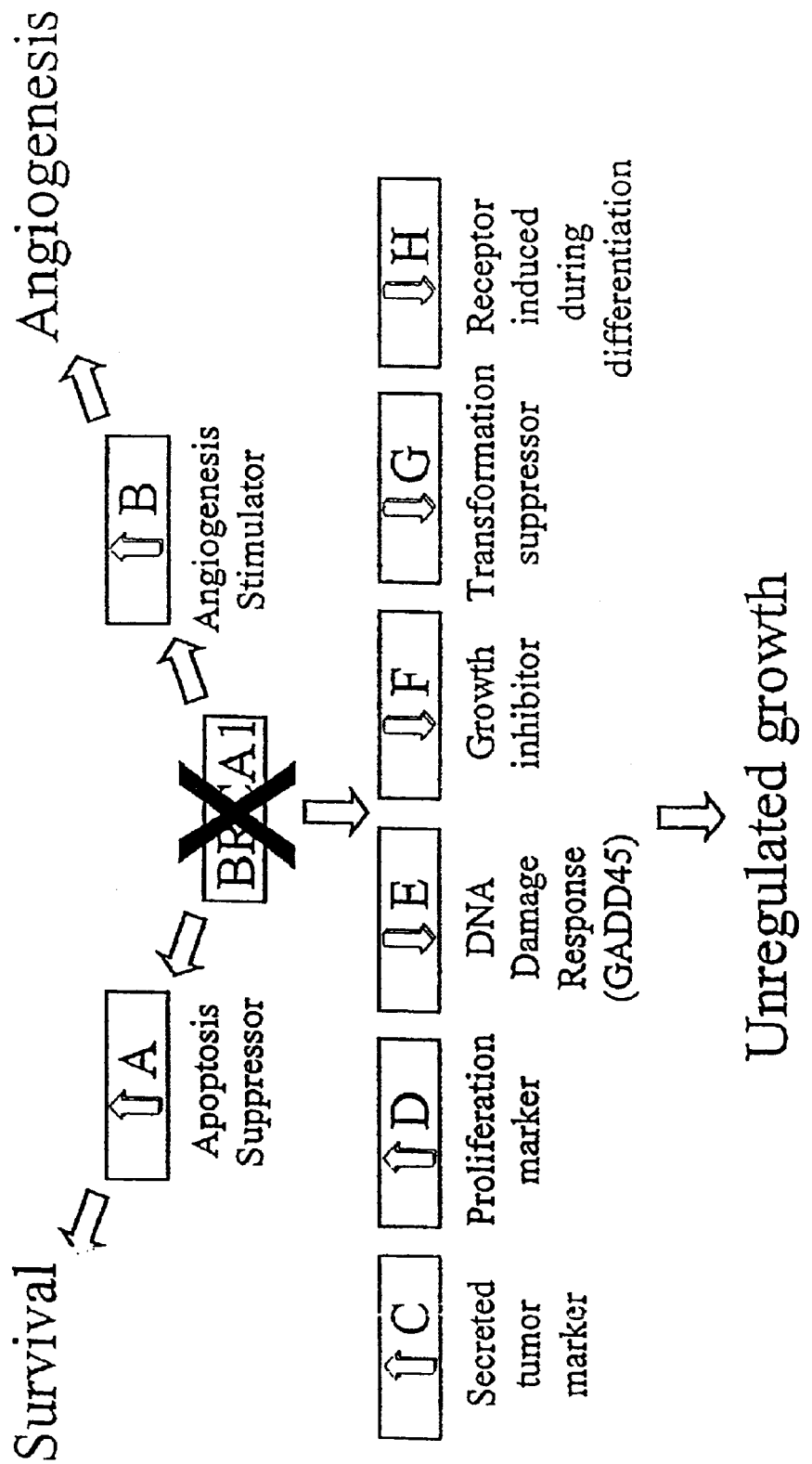
FIG. 1 displays proposed mechanistic advantages of BRCA1 inactivation. Gens A to H display reproducibly altered expression patterns following BRCA1 induction. Arrows pointing up indicate increases in expression, and arrows pointing down indicate decreases in expression. The directionality of these arrrows is opposite to that of the expression changes observed following BRCA1 induction; they are meant to indicate the putative effects of BRCA1 inactivation.

The present invention is directed to the systematic analysis of relationships between expression patterns of genes affected by other genes. This approach represents a paradigm shift away from research efforts focusing on single genes in isolation and towards integrated analyses of multiple-gene networks. While the effect of any gene on any other gene can be studied, the methods are particularly useful for analyzing the effects of tumor suppressor genes and oncogenes.

Any means known in the art can be utilized for altering the expression of putative effector genes. In one exemplary means a cell which is null for the putative effector gene is compared to an isogenic cell which is wild-type for the effector gene. In another exemplary means cells are used which contain a transgene under the control of an exogenously regulated promoter. Two populations of the exogenously regulatable cells are compared: cells which are treated so that the transgene is expressed, and cells which are treated so that the transgene is not expressed. Other means for altering expression of a putative effector gene include mutagenizing the putative effector gene, administering antisense oligonucleotides or antisense-expressing constructs to cells to inhibit translation of the mRNA of the putative effector gene, administering ribozymes or ribozyme-expressing constructs to cells to inhibit translation of the mRNA of the putative effector gene, and altering copy number of the putative effector gene. Techniques for accomplishing these means of altered expression are well known in the art and any can be used as is desirable and convenient.

The methods disclosed herein model the networks of genes as combinatorial objects, with finite simple functions leading between genes with discrete states. This is a fundamentally computational and combinatorial approach, which explicitly deals with interactions within a network and requires no time-series data. Since we are making single, simple modifications to genes, and can reliably detect changes in thousands of putative effected genes using only a few experiments, our methodology is combinatorial in nature. This permits us to trace the flow of signal information down pathways, and hence our problem is tractable with relatively few data collection events.

Cell lines harboring single alterations in genes known or unknown to reside in common pathways can be used. Pathway modeling algorithms recognize links among the products of these genes and order these products within regulatory cascades. Model regulatory systems which involve genes that act in pathways targeted for mutation during tumorigenesis can be used, for example. Specifically, we can compare the expression profiles of cell lines that differ from one another only by 1) the introduction of a single inducible transgene, or by 2) the deletion of a single endogenous gene. As discussed above, other alterations can also be used to effect expression of a single gene. Any attendant expression changes can be attributed to a unique genetic change, i.e., to the alteration of the single gene. Expression profiles for thousands of genes can be obtained simultaneously by hybridizing labeled RNA (or derived cDNA) from these cell lines to high-density oligonucleotide arrays. Other methods known in the art for obtaining expression data of multiple genes can also be used, including the Serial Analysis of Gene Expression technique. See U.S. Pat. No. 5,695,937.

Transgenes can be introduced into cells or animals. The cells or animals may or may not lack those genes. For example, a cell which lacks p53 can be supplied with a p53 transgene from another cell or animal. Alternatively, additional gene copy number can be achieved by introducing an additional copy of a gene to a cell or animal which contains the gene. Thus transgenes need not be from other species, although they can be. Cells which are lacking the genes can be naturally so or experimentally induced. The "lack" can be genetic (mutation) or phenotypic (inhibition of expression or activity by another gene product).

Exogenously regulatable promoters can be used to alter expression of the effector genes; these can be inducible or repressible. The effector of regulation can be a chemical, e.g., a hormone or drug, or another agent such as γ-irradiation which can be controlled experimentally. Treatment to permit transcription or to permit no transcription can be active or passive. Thus not applying an agent can constitute "treatment" to achieve a certain transcriptional state.

Mutagenesis can be used to alter expression of a selected gene. Any means known in the art can be used, although controlled methods are preferred to eliminate the possibility of multiple mutations, especially those in other genes.

Antisense constructs or oligonucleotides and ribozyme constructs or oligonucleotides can also be used to alter expression of a selected gene. Methods for making and administering these agents are also well known, and any such methods can be used in the context of the present invention for altering expression.

Determining expression levels can be done by observing, quantitatively or qualitatively, expression of a gene product. The gene product can be mRNA or protein. The actual gene product can be observed or some derivative, such as cDNA. Protein can be observed by any means known in the art, including immunological methods and enzyme assays. Any method for observing gene expression can be used, without limitation. Absolute measurements of the expression levels need not be made, although they can be made. Comparisons of differences in expression levels is, however, required. A preferred method utilizes the simultaneous analysis of expression of multiple genes, such as using the Serial Analysis of Gene Expression (SAGE) method or using hybridization to DNA arrays.

Comparison of expression levels can be done visually or manually, or may be automated and done by a machine, using for example optical detection means. Hardware and software for analyzing differential expression of a gene are available, and may be used in practicing the present invention.

Once a candidate functional mediator (CFM) is identified, it can be used in an iterative fashion as an effector gene to determine the effect that it has on other (downstream) genes. The CFM becomes a selected gene which is the target of expression altering treatment. Thus, for example, exogenously regulatable constructs can be made using the CFM, or mutant cells null for the CFM can be used. This can be done repeatedly to "work down the pathway", or it can be done for multiple CFMs identified to expand into branches of the pathway.

Any gene can be used in the present invention as a selected gene (an effector gene), e.g., as a transgene or as a mutated null gene. Tumor genes or oncogenes are particularly interesting, but the invention is not limited to the type of gene used. The methods do not rely on function of the gene product, thus the function is not a limitation.

The methods of the invention permit the ordering of effector genes relative to each other in a pathway. It also permits the identification of and ordering of candidate functional mediator genes in a pathway. Comparing sets of effected genes and finding overlaps in the sets and non-overlaps in the sets permits the reconstruction of pathways. The pathways indicate which gene products influence the expression of other gene products.

This invention provides methods for interrogating the genetic network. The methods involve quantifying the level of expression of a large number of genes. In some preferred embodiments, a high density oligonucleotide array is used to hybridize with a target nucleic acid sample to detect the expression level of a large number of genes, preferably more than 10, more preferably more than 100, and most preferably more than 1000 genes.

Activity of a gene is reflected by the activity of its products): the proteins or other molecules encoded by the gene. Those product molecules perform biological functions. Directly measuring the activity of a gene product is, however, often difficult for certain genes. Instead, the immunological activities or the amount of the final product(s) or its peptide processing intermediates are determined as a measurement of the gene activity. More frequently, the amount or activity of intermediates, such as transcripts, RNA processing intermediates, or mature mRNAs are detected as a measurement of gene activity.

In many cases, the form and function of the final product (s) of a gene is unknown. In those cases, the activity of a gene is measured conveniently by the amount or activity of transcript(s), RNA processing intermediate(s), mature mRNA(s) or its protein product(s) or functional activity of its protein product(s).

Any methods that measure the activity of a gene are useful for at least some embodiments of this invention. For example, traditional Northern blotting and hybridization, nuclease protection, RT-PCR and differential display have been used for detecting gene activity. Those methods are useful for some embodiments of the invention. However, this invention is most useful in conjunction with methods for detecting the expression of a large number of genes.

High density arrays are particularly useful for monitoring the expression control at the transcriptional, RNA processing and degradation level. The fabrication and application of high density arrays in gene expression monitoring have been disclosed previously in, for example, WO 97/10365, WO 92/10588, U.S. application Ser. No. 08/772,376 filed Dec. 23, 1996; Ser. No. 08/529,115 filed on Sep. 15, 1995; Ser. No. 08/168,904 filed Dec. 15, 1993; Ser. No. 07/624,114 filed on Dec. 6, 1990, Ser. No. 07/362,901 filed Jun. 7, 1990, all incorporated herein for all purposes by reference. In some embodiments using high density arrays, high density oligonucleotide arrays are synthesized using methods such as the Very Large Scale Immobilized Polymer Synthesis (VLSIPS) disclosed in U.S. Pat. No. 5,445,934 incorporated herein for all purposes by reference. Each oligonucleotide occupies a known location on a substrate. A nucleic acid target sample is hybridized with a high density array of oligonucleotides and then the amount of target nucleic acids hybridized to each probe in the array is quantified. One preferred quantifying method is to use confocal microscope and fluorescent labels. The GeneChip® system (Affymetrix, Santa Clara, Calif.) is particularly suitable for quantifying the hybridization; however, it will be apparent to those of skill in the art that any similar systems or other effectively equivalent detection methods can also be used.

High density arrays are suitable for quantifying a small variations in expression levels of a gene in the presence of a large population of heterogeneous nucleic acids. Such high density arrays can be fabricated either by de novo synthesis on a substrate or by spotting or transporting nucleic acid sequences onto specific locations of substrate. Nucleic acids are purified and/or isolated from biological materials, such as a bacterial plasmid containing a cloned segment of sequence of interest. Suitable nucleic acids are also produced by amplification of templates. As a nonlimiting illustration, polymerase chain reaction, and/or in vitro transcription, are suitable nucleic acid amplification methods.

Synthesized oligonucleotide arrays are particularly preferred for this invention. Oligonucleotide arrays have numerous advantages, as opposed to other methods, such as efficiency of production, reduced intra- and inter array variability, increased information content and high signal-to-noise ratio.

Preferred high density arrays for gene function identification and genetic network mapping comprise greater than about 100, preferably greater than about 1000, more preferably greater than about 16,000 and most preferably greater than 65,000 or 250,000 or even greater than about 1,000,000 different oligonucleotide probes, preferably in less than 1 cm² of surface area The oligonucleotide probes range from about 5 to about 50 or about 500 nucleotides, more preferably from about 10 to about 40 nucleotide and most preferably from about 15 to about 40 nucleotides in length.

Massive Parallel Gene Expression Monitoring

One preferred method for massive parallel gene expression monitoring is based upon high density nucleic acid arrays. Nucleic acid array methods for monitoring gene expression are disclosed and discussed in detail in PCT Application WO 092.10588 (published on Jun. 25, 1992), all incorporated herein by reference for all purposes.

Generally those methods of monitoring gene expression involve (a) providing a pool of target nucleic acids comprising RNA transcript(s) of one or more target gene(s), or nucleic acids derived from the RNA transcript(s); (b) hybridizing the nucleic acid sample to a high density array of probes and (c) detecting the hybridized nucleic acids and calculating a relative and/or absolute expression (transcription, RNA processing or degradation) level.

(A) Providing a Nucleic Acid Sample

One of skill in the art will appreciate that it is desirable to have nucleic samples containing target nucleic acid sequences that reflect the transcripts of interest. Therefore, suitable nucleic acid samples may contain transcripts of interest. Suitable nucleic acid samples, however, may contain nucleic acids derived from the transcripts of interest. As used herein, a nucleic acid derived from a transcript refers to a nucleic acid for whose synthesis the mRNA transcript or a subsequence thereof has ultimately served as a template. Thus, a cDNA reverse transcribed from a transcript, an RNA transcribed from that cDNA, a DNA amplified from the cDNA, an RNA transcribed from the amplified DNA, etc., are all derived from the transcript and detection of such derived products is indicative of the presence and/or abundance of the original transcript in a sample. Thus, suitable samples include, but are not limited to, transcripts of the gene or genes, cDNA reverse transcribed from the transcript, cRNA transcribed from the cDNA, DNA amplified from the genes, RNA transcribed from amplified DNA, and the like.

Transcripts, as used herein, may include, but not limited to pre-mRNA nascent transcript(s), transcript processing intermediates, mature mRNA(s) and degradation products. It is not necessary to monitor all types of transcripts to practice this invention. For example, one may choose to practice the invention to measure the mature mRNA levels only.

In one embodiment, such sample is a homogenate of cells or tissues or other biological samples. Preferably, such sample is a total RNA preparation of a biological sample. More preferably in some embodiments, such a nucleic acid sample is the total mRNA isolated from a biological sample. Those of skill in the art will appreciate that the total mRNA prepared with most methods includes not only the mature mRNA, but also the RNA processing intermediates and nascent pre-mRNA transcripts. For example, total mRNA purified with a poly (dT) column contains RNA molecules with poly (A) tails. Those polyA⁺ RNA molecules could be mature mRNA, RNA processing intermediates, nascent transcripts or degradation intermediates.

Biological samples may be of any biological tissue or fluid or cells from any organism. Frequently the sample will be a "clinical sample" which is a sample derived from a patient. Clinical samples provide a rich source of information regarding the various states of genetic network or gene expression. Some embodiments of the invention are employed to detect mutations and to identify the phenotype of mutations. Such embodiments have extensive applications in clinical diagnostics and clinical studies. Typical clinical samples include, but are not limited to, sputum, blood, blood cells (e.g., white cells), tissue or fine needle biopsy samples, urine, peritoneal fluid, and pleural fluid, or cells therefrom. Biological samples may also include sections of tissues, such as frozen sections or formalin fixed sections taken for histological purposes.

Another typical source of biological samples are cell cultures where gene expression states can be manipulated to explore the relationship among genes. In one aspect of the invention, methods are provided to generate biological samples reflecting a wide variety of states of the genetic network.

One of skill in the art would appreciate that it is desirable to inhibit or destroy RNase present in homogenates before homogenates can be used for hybridization. Methods of inhibiting or destroying nucleases are well known in the art. In some preferred embodiments, cells or tissues are homogenized in the presence of chaotropic agents to inhibit nuclease. In some other embodiments, RNase is inhibited or destroyed by heat treatment followed by proteinase treatment Methods of isolating total mRNA are also well known to those of skill in the art. For example, methods of isolation and purification of nucleic acids are described in detail in Chapter 3 of *Laboratory Techniques in Biochemistry and Molecular Biology: Hybridization With Nucleic Acid Probes*, Part I. *Theory and Nucleic Acid Preparation*, P. Tijssen, ed. Elsevier, N.Y. (1993) and Chapter 3 of *Laboratory Techniques* in *Biochemistry and Molecular Biology: Hybridization With Nucleic Acid Probes*, Part I. *Theory and Nucleic Acid Preparation*, P. Tijssen, ed. Elsevier, N.Y. (1993)).

In a preferred embodiment, the total RNA is isolated from a given sample using, for example, an acid guanidinium-phenol-chloroform extraction method and polyA⁺ mRNA is isolated by oligo(dT) column chromatography or by using (dT) on magnetic beads (see, e.g., Sambrook et al, *Molecular Cloning: A Laboratory Manual* (2nd ed.), Vols. 1–3, Cold Spring Harbor Laboratory, (1989), or *Current Protocols in Molecular Biology*, F. Ausubel et al, ed. Greene Publishing and Wiley-Interscience, New York (1987)).

Frequently, it is desirable to amplify the nucleic acid sample prior to hybridization. One of skill in the art will appreciate that whatever amplification method is used, if a quantitative result is desired, care must be taken to use a method that maintains or controls for the relative frequencies of the amplified nucleic acids to achieve quantitative amplification.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. The high density array may then include probes specific to the internal standard for quantification of the amplified nucleic acid.

One preferred internal standard is a synthetic AW106 cRNA. The AW106 cRNA is combined with RNA isolated from the sample according to standard techniques known to those of skilled in the art. The RNA is then reverse transcribed using a reverse transcriptase to provide copy DNA. The cDNA sequences are then amplified (e.g., by PCR) using labeled primers. The amplification products are separated, typically by electrophoresis, and the amount of radioactivity (proportional to the amount of amplified product) is determined. The amount of mRNA in the sample is then calculated by-comparison with the signal produced by the known AW106 RNA standard. Detailed protocols for quantitative PCR are provided in *PCR Protocols, A Guide to Methods and Applications*, Innis et al., Academic Press, Inc. N.Y., (1990).

Other suitable amplification methods include, but are not limited to polymerase chain reaction (PCR) (Innis, et al., *PCR Protocols. A guide to Methods and Application*. Academic Press, Inc. San Diego, (1990)), ligase chain reaction (LCR) (see Wu and Wallace, *Genomics*, 4: 560 (1989), Landegren, et al., *Science*, 241: 1077 (1988) and Barringer, et al., *Gene*, 89: 117 (1990), transcription amplification (Kwoh, et al., *Proc. Natl. Acad. Sci. USA*, 86: 1173 (1989)), and self-sustained sequence replication (Guatelli, et al., *Proc. Nat. Acad. Sci. USA*, 87: 1874 (1990)).

Cell lysates or tissue homogenates often contain a number of inhibitors of polymerase activity. Therefore, RT-PCR typically incorporates preliminary steps to isolate total RNA or mRNA for subsequent use as an amplification template. A one-tube mRNA capture method may be used to prepare poly(A)$^+$ RNA samples suitable for immediate RT-PCR in the same tube (Boehringer Mannheim). The captured mRNA can be directly subjected to RT-PCR by adding a reverse transcription mix and, subsequently, a PCR mix.

In a particularly preferred embodiment, the sample mRNA is reverse transcribed with a reverse transcriptase and a primer consisting of oligo(dT) and a sequence encoding the phage T7 promoter to provide single stranded DNA template. The second DNA strand is polymerized using a DNA polymerase. After synthesis of double-stranded cDNA, T7 RNA polymerase is added and RNA is transcribed from the cDNA template. Successive rounds of transcription from each single cDNA template results in amplified RNA. Methods of in vitro polymerization are well known to those of skill in the art (see, e.g., Sambrook, supra.) and this particular method is described in detail by Van Gelder, et al., *Proc. Natl. Acad. Sci. USA*, 87: 1663–1667 (1990) who demonstrate that in vitro amplification according to this method preserves the relative frequencies of the various RNA transcripts. Moreover, Eberwine et al. *Proc. Natl. Acad. Sci. USA*, 89: 3010–3014 provide a protocol that uses two rounds of amplification via in vitro transcription to achieve greater than $10^6$ fold amplification of the original starting material, thereby permitting expression monitoring even where biological samples are limited.

It will be appreciated by one of skill in the art that the direct transcription method described above provides an antisense (aRNA) pool. Where antisense RNA is used as the target nucleic acid, the oligonucleotide probes provided in the array are chosen to be complementary to subsequences of the antisense nucleic acids. Conversely, where the target nucleic acid pool is a pool of sense nucleic acids, the oligonucleotide probes are selected to be complementary to subsequences of the sense nucleic acids. Finally, where the nucleic acid pool is double stranded, the probes may be of either sense as the target nucleic acids include both sense and antisense strands.

The protocols cited above include methods of generating pools of either sense or antisense nucleic acids. Indeed, one approach can be used to generate either sense or antisense nucleic acids as desired. For example, the cDNA can be directionally cloned into a vector (e.g., Stratagene's p Bluscript II KS (+) phagemid) such that it is flanked by the T3 and T7 promoters. In vitro transcription with the T3 polymerase will produce RNA of one sense (the sense depending on the orientation of the insert), while in vitro transcription with the T7 polymerase will produce RNA having the opposite sense. Other suitable cloning systems include phage lambda vectors designed for Cre-loxP plasmid subcloning (see e.g., Palazzolo et al., *Gene*, 88: 25–36 (1990)).

(B) Hybridizing Nucleic Acids to High Density Arrays

1. Probe Design

One of skill in the art will appreciate that an enormous number of array designs are suitable for the practice of this invention. The high density array will typically include a number of probes that specifically hybridize to the sequences of interest. In addition, in a preferred embodiment, the array will include one or more control probes.

The high density array chip includes "test probes." Test probes could be oligonucleotides that range from about 5 to about 45 or 5 to about 500 nucleotides, more preferably from about 10 to about 40 nucleotides and most preferably from about 15 to about 40 nucleotides in length. In other particularly preferred embodiments the probes are 20 or 25 nucleotides in length. In another preferred embodiments, test probes are double or single strand DNA sequences. DNA sequences are isolated or cloned from nature sources or amplified from nature sources using nature nucleic acid as templates. These probes have sequences complementary to particular subsequences of the genes whose expression they are designed to detect. Thus, the test probes are capable of specifically hybridizing to the target nucleic acid they are to detect.

In addition to test probes that bind the target nucleic acid(s) of interest, the high density array can contain a number of control probes. The control probes fall into three categories referred to herein as 1) normalization controls; 2) expression level controls; and 3) mismatch controls.

Normalization controls are oligonucleotide or other nucleic acid probes that are complementary to labeled reference oligonucleotides or other nucleic acid sequences that are added to the nucleic acid sample. The signals obtained from the normalization controls after hybridization provide a control for variations in hybridization conditions, label intensity, "reading" efficiency and other factors that may cause the signal of a perfect hybridization to vary between arrays. In a preferred embodiment, signals (e.g., fluorescence intensity) read from all other probes in the array are divided by the signal (e.g., fluorescence intensity) from the control probes thereby normalizing the measurements.

Virtually any probe may serve as a normalization control. However, it is recognized that hybridization efficiency varies with base composition and probe length. Preferred normalization probes are selected to reflect the average length of the other probes present in the array, however, they can be selected to cover a range of lengths. The normalization control(s) can also be selected to reflect the (average) base composition of the other probes in the array, however in a preferred embodiment, only one or a few normalization probes are used and they are selected such that they hybridize well (i.e. no secondary structure) and do not match any target-specific probes.

Expression level controls are probes that hybridize specifically with constitutively expressed genes in the biological sample. Virtually any constitutively expressed gene provides a suitable target for expression level controls. Typically expression level control probes have sequences complementary to subsequences of constitutively expressed "housekeeping genes" including, but not limited to the β-actin gene, the transferrin receptor gene, the GAPDH gene, and the like.

Mismatch controls may also be provided for the probes to the target genes, for expression level controls or for normalization controls. Mismatch controls are oligonucleotide probes or other nucleic acid probes identical to their corresponding test or control probes except for the presence of one or more mismatched bases. A mismatched base is a base selected so that it is not complementary to the corresponding base in the target sequence to which the probe would otherwise specifically hybridize. One or more mismatches are selected such that under appropriate hybridization conditions (e.g. stringent conditions) the test or control probe would be expected to hybridize with its target sequence, but the mismatch probe would not hybridize (or would hybridize to a significantly lesser extent). Preferred mismatch probes contain a central mismatch. Thus, for example, where a probe is a 20 mer, a corresponding mismatch probe will have the identical sequence except for a single base mismatch (e.g., substituting a G, a C or a T for an A) at any of positions 6 through 14 (the central mismatch).

Mismatch probes thus provide a control for non-specific binding or cross-hybridization to a nucleic acid in the sample other than the target to which the probe is directed. Mismatch probes thus indicate whether a hybridization is specific or not. For example, if the target is present the perfect match probes should be consistently brighter than the mismatch probes. In addition, if all central mismatches are present, the mismatch probes can be used to detect a mutation. The difference in intensity between the perfect match and the mismatch probe (I(PM)-I(MM)) provides a good measure of the concentration of the hybridized material.

The high density array may also include sample preparation/amplification control probes. These are probes that are complementary to subsequences of control genes selected because they do not normally occur in the nucleic acids of the particular biological sample being assayed. Suitable sample preparation/amplification control probes include, for example, probes to bacterial genes (e.g., Bio B) where the sample in question is a biological from a eukaryote.

The RNA sample is then spiked with a known amount of the nucleic acid to which the sample preparation/amplification control probe is directed before processing. Quantification of the hybridization of the sample preparation/amplification control probe then provides a measure of alteration in the abundance of the nucleic acids caused by processing steps (e.g. PCR, reverse transcription, in vitro transcription, etc.).

In a preferred embodiment, oligonucleotide probes in the high density array are selected to bind specifically to the nucleic acid target to which they are directed with minimal non-specific binding or cross-hybridization under the particular hybridization conditions utilized. Because the high density arrays of this invention can contain in excess of 1,000,000 different probes, it is possible to provide every probe of a characteristic length that binds to a particular nucleic acid sequence. Thus, for example, the high density array can contain every possible 20-mer sequence complementary to an IL-2 mRNA.

However, there may exist 20-mer subsequences that are not unique to the IL-2 mRNA. Probes directed to these subsequences are expected to cross-hybridize with occurrences of their complementary sequence in other regions of the sample genome. Similarly, other probes simply may not hybridize effectively under the hybridization conditions (e.g., due to secondary structure, or interactions with the substrate or other probes). Thus, in a preferred embodiment, the probes that show such poor specificity or hybridization efficiency are identified and may not be included either in the high density array itself (e.g., during fabrication of the array) or in the post-hybridization data analysis.

In addition, in a preferred embodiment, expression monitoring arrays are used to identify the presence and expression (transcription) level of genes which are several hundred base pairs long. For most applications it would be useful to identify the presence, absence, or expression level of several thousand to one hundred thousand genes. Because the number of oligonucleotides per array is limited in a preferred embodiment, it is desired to include only a limited set of probes specific to each gene whose expression is to be detected.

As disclosed in U.S. application Ser. No. 08/772,376, probes as short as 15, 20, or 25 nucleotide are sufficient to hybridize to a subsequence of a gene and that, for most genes, there is a set of probes that performs well across a wide range of target nucleic acid concentrations. In a preferred embodiment, it is desirable to choose a preferred or "optimum" subset of probes for each gene before synthesizing the high density array.

2. Forming High Density Arrays.

Methods of forming high density arrays of oligonucleotides, peptides and other polymer sequences with a minimal number of synthetic steps are known. The oligonucleotide analogue array can be synthesized on a solid substrate by a variety of methods, including, but not limited to, light-directed chemical coupling, and mechanically directed coupling. See Pirrung et al., U.S. Pat. No. 5,143,854 (see also PCT Application No. WO 90/15070) and Fodor et al., PCT Publication Nos. WO 92/10092 and WO 93/09668 and U.S. Ser. No. 07/980,523 which disclose methods of forming vast arrays of peptides, oligonucleotides and other molecules using, for example, light-directed synthesis techniques. See also, Fodor et al., *Science*, 251, 767–77 (1991). These procedures for synthesis of polymer arrays are now referred to as VLSIPS™ procedures. Using the VLSIPS™ approach, one heterogeneous array of polymers is converted, through simultaneous coupling at a number of reaction sites, into a different heterogeneous array. See, U.S. application Ser. Nos. 07/796,243 and 07/980,523.

The development of VLSIPS™ technology as described in the above-noted U.S. Pat. No. 5,143,854 and PCT patent publication Nos. WO 90/15070 and 92/10092, is considered pioneering technology in the fields of combinatorial synthesis and screening of combinatorial libraries. More recently, patent application Ser. No. 08/082,937, filed Jun. 25, 1993, describes methods for making arrays of oligonucleotide probes that can be used to check or determine a partial or complete sequence of a target nucleic acid and to detect the presence of a nucleic acid containing a specific oligonucleotide sequence.

In brief, the light-directed combinatorial synthesis of oligonucleotide arrays on a glass surface proceeds using automated phosphoramidite chemistry and chip masking techniques. In one specific implementation, a glass surface is derivatized with a silane reagent containing a functional group, e.g., a hydroxyl or amine group blocked by a photolabile protecting group. Photolysis through a photolithographic mask is used selectively to expose functional groups which are then ready to react with incoming 5'-photoprotected nucleoside phosphoramidites. The phosphoramidites react only with those sites which are illuminated (and thus exposed by removal of the photolabile blocking group). Thus, the phosphoramidites only add to those areas selectively exposed from the preceding step. These steps are repeated until the desired array of sequences have been synthesized on the solid surface. Combinatorial synthesis of different oligonucleotide analogues at different locations on the array is determined by the pattern of illumination during synthesis and the order of addition of coupling reagents.

In the event that an oligonucleotide analogue with a polyamide backbone is used in the VLSIPS™ procedure, it is generally inappropriate to use phosphoramidite chemistry to perform the synthetic steps, since the monomers do not attach to one another via a phosphate linkage. Instead, peptide synthetic methods are substituted. See, e.g., Pirrung et al. U.S. Pat. No. 5,143,854.

Peptide nucleic acids are commercially available from, e.g., Biosearch, Inc. (Bedford, Mass.) which comprise a polyamide backbone and the bases found in naturally occurring nucleosides. Peptide nucleic acids are capable of binding to nucleic acids with high specificity, and are considered "oligonucleotide analogues" for purposes of this disclosure.

In addition to the foregoing, additional methods which can be used to generate an array of oligonucleotides on a single substrate are described in co-pending applications Ser. No. 07/980,523, filed Nov. 20, 1992, and Ser. No. 07/796,243, filed Nov. 22, 1991 and in PCT Publication No. WO 93/09668. In the methods disclosed in these applications, reagents are delivered to the substrate by either (1) flowing within a channel defined on predefined regions or (2) "spotting" on predefined regions or (3) through the use of photoresist. However, other approaches, as well as combinations of spotting and flowing, may be employed. In each instance, certain activated regions of the substrate are mechanically separated from other regions when the monomer solutions are delivered to the various reaction sites.

A typical "flow channel" method applied to the compounds and libraries of the present invention can generally be described as follows. Diverse polymer sequences are synthesized at selected regions of a substrate or solid support by forming flow channels on a surface of the substrate through which appropriate reagents flow or in which appropriate reagents are placed. For example, assume a monomer "A" is to be bound to the substrate in a first group of selected regions. If necessary, all or part of the surface of the substrate in all or a part of the selected regions is activated for binding by, for example, flowing appropriate reagents through all or some of the channels, or by washing the entire substrate with appropriate reagents. After placement of a channel block on the surface of the substrate, a reagent having the monomer A flows through or is placed in all or some of the channel(s). The channels provide fluid contact to the first selected regions, thereby binding the monomer A on the substrate directly or indirectly (via a spacer) in the first selected regions.

Thereafter, a monomer B is coupled to second selected regions, some of which may be included among the first selected regions. The second selected regions will be in fluid contact with a second flow channel(s) through translation, rotation, or replacement of the channel block on the surface of the substrate; through opening or closing a selected valve; or through deposition of a layer of chemical or photoresist. If necessary, a step is performed for activating at least the second regions. Thereafter, the monomer B is flowed through or placed in the second flow channel(s), binding monomer B at the second selected locations. In this particular example, the resulting sequences bound to the substrate at this stage of processing will be, for example, A, B, and AB. The process is repeated to form a vast array of sequences of desired length at known locations on the substrate.

After the substrate is activated, monomer A can be flowed through some of the channels, monomer B can be flowed through other channels, a monomer C can be flowed through still other channels, etc. In this manner, many or all of the reaction regions are reacted with a monomer before the channel block must be moved or the substrate must be washed and/or reactivated. By making use of many or all of the available reaction regions simultaneously, the number of washing and activation steps can be minimized.

One of skill in the art will recognize that there are alternative methods of forming channels or otherwise protecting a portion of the surface of the substrate. For example, according to some embodiments, a protective coating such as a hydrophilic or hydrophobic coating (depending upon the nature of the solvent) is utilized over portions of the substrate to be protected, sometimes in combination with materials that facilitate wetting by the reactant solution in other regions. In this manner, the flowing solutions are further prevented from passing outside of their designated flow paths.

High density nucleic acid arrays can be fabricated by depositing presynthezied or natural nucleic acids in predined positions. Synthesized or natural nucleic acids are deposited on specific locations of a substrate by light directed targeting and oligonucleotide directed targeting. Nucleic acids can also be directed to specific locations in much the same manner as the flow channel methods. For example, a nucleic acid A can be delivered to and coupled with a first group of reaction regions which have been appropriately activated. Thereafter, a nucleic acid B can be delivered to and reacted with a second group of activated reaction regions. Nucleic acids are deposited in selected regions. Another embodiment uses a dispenser that moves from region to region to deposit nucleic acids in specific spots. Typical dispensers include a micropipette or capillary pin to deliver nucleic acid to the substrate and a robotic system to control the position of the micropipette with respect to the substrate. In other embodiments, the dispenser includes a series of tubes, a manifold, an array of pipettes or capillary pins, or the like so that various reagents can be delivered to the reaction regions simultaneously.

3. Hybridization

Nucleic acid hybridization simply involves contacting a probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

One of skill in the art will appreciate that hybridization conditions may be selected to provide any degree of stringency. In a preferred embodiment, hybridization is performed at low stringency in this case in 6×SSPE-T at 37 C (0.005% Triton X-100) to ensure hybridization and then subsequent washes are performed at higher stringency (e.g., 1×SSPE-T at 37 C) to eliminate mismatched hybrid duplexes. Successive washes may be performed at increasingly higher stringency (e.g., down to as low as 0.25× SSPE-T at 37 C to 50 C) until a desired level of hybridization specificity is obtained. Stringency can also be increased by addition of agents such as formamide. Hybridization specificity may be evaluated by comparison of hybridization to the test probes with hybridization to the various controls that can be present (e.g., expression level control, normalization control, mismatch controls, etc.).

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above which the hybridization pattern is not appreciably altered and which provides adequate signal for the particular oligonucleotide probes of interest.

In a preferred embodiment, background signal is reduced by the use of a detergent (e.g., C-TAB) or a blocking reagent (e.g., sperm DNA, cot-1 DNA, etc.) during the hybridization to reduce non-specific binding. In a particularly preferred embodiment, the hybridization is performed in the presence of about 0.5 mg/ml DNA (e.g., herring sperm DNA). The use of blocking agents in hybridization is well known to those of skill in the art (see, e.g., Chapter 8 in P. Tijssen, supra.)

The stability of duplexes formed between RNAs or DNAs are generally in the order of RNA:RNA>RNA:DNA>DNA:DNA, in solution. Long probes have better duplex stability with a target, but poorer mismatch discrimination than shorter probes (mismatch discrimination refers to the measured hybridization signal ratio between a perfect match probe and a single base mismatch probe). Shorter probes (e.g., 8-mers) discriminate mismatches very well, but the overall duplex stability is low.

Altering the thermal stability ($T_m$) of the duplex formed between the target and the probe using, e.g., known oligonucleotide analogues allows for optimization of duplex stability and mismatch discrimination. One useful aspect of altering the $T_m$ arises from the fact that adenine-thymine (A-T) duplexes have a lower $T_m$ than guanine-cytosine (G-C) duplexes, due in part to the fact that the A-T duplexes have 2 hydrogen bonds per base-pair, while the G-C duplexes have 3 hydrogen bonds per base pair. In heterogeneous oligonucleotide arrays in which there is a non-uniform distribution of bases, it is not generally possible to optimize hybridization for each oligonucleotide probe simultaneously. Thus, in some embodiments, it is desirable to selectively destabilize G-C duplexes and/or to increase the stability of A-T duplexes. This can be accomplished, e.g., by substituting guanine residues in the probes of an array which form G-C duplexes with hypoxanthine, or by substituting adenine residues in probes which form A-T duplexes with 2,6 diaminopurine or by using the salt tetramethyl ammonium chloride (TMAC1) in place of NaCl.

Altered duplex stability conferred by using oligonucleotide analogue probes can be ascertained by following, e.g., fluorescence signal intensity of oligonucleotide analogue arrays hybridized with a target oligonucleotide over time. The data allow optimization of specific hybridization conditions at, e.g., room temperature (for simplified diagnostic applications in the future).

Another way of verifying altered duplex stability is by following the signal intensity generated upon hybridization with time. Previous experiments using DNA targets and DNA chips have shown that signal intensity increases with time, and that the more stable duplexes generate higher signal intensities faster than less stable duplexes. The signals reach a plateau or "saturate" after a certain amount of time due to all of the binding sites becoming occupied. These data allow for optimization of hybridization, and determination of the best conditions at a specified temperature.

Methods of optimizing hybridization conditions are well known to those of skill in the art (see, e.g., *Laboratory Techniques in Biochemistry and Molecular Biology*, Vol. 24: *Hybridization With Nucleic Acid Probes*, P. Tijssen, ed. Elsevier, N.Y., (1993)).

(C) Signal Detection

In a preferred embodiment, the hybridized nucleic acids are detected by detecting one or more labels attached to the sample nucleic acids. The labels may be incorporated by any of a number of means well known to those of skill in the art. However, in a preferred embodiment, the label is simultaneously incorporated during the amplification step in the preparation of the sample nucleic acids. Thus, for example, polymerase chain reaction (PCR) with labeled primers or labeled nucleotides will provide a labeled amplification product. In a preferred embodiment, transcription amplification, as described above, using a labeled nucleotide (e.g. fluorescein-labeled UTP and/or CTP) incorporates a label into the transcribed nucleic acids.

Alternatively, a label may be added directly to the original nucleic acid sample (e.g., mRNA, polyA mRNA, cDNA, etc.) or to the amplification product after the amplification is completed. Means of attaching labels to nucleic acids are well known to those of skill in the art and include, for example nick translation or end-labeling (e.g. with a labeled RNA) by kinasing of the nucleic acid and subsequent attachment (ligation) of a nucleic acid linker joining the sample nucleic acid to a label (e.g., a fluorophore).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label. One particular preferred methods uses colloidal gold label that can be detected by measuring scattered light.

The label may be added to the target (sample) nucleic acid(s) prior to, or after the hybridization. So called "direct labels" are detectable labels that are directly attached to or incorporated into the target (sample) nucleic acid prior to hybridization. In contrast, so called "indirect labels" are joined to the hybrid duplex after hybridization Often, the indirect label is attached to a binding moiety that has been attached to the target nucleic acid prior to the hybridization. Thus, for example, the target nucleic acid may be biotinylated before the hybridization. After hybridization, an aviden-conjugated fluorophore will bind the biotin bearing hybrid duplexes providing a label that is easily detected. For a detailed review of methods of labeling nucleic acids and detecting labeled hybridized nucleic acids see *Laboratory Techniques in Biochemistry and Molecular Biology*, Vol. 24: *Hybridization With Nucleic Acid Probes*, P. Tijssen, ed. Elsevier, N.Y., (1993)).

Fluorescent labels are preferred and easily added during an in vitro transcription reaction. In a preferred embodiment, fluorescein labeled UTP and CTP are incorporated into the RNA produced in an in vitro transcription reaction as described above.

Means of detecting labeled target (sample) nucleic acids hybridized to the probes of the high density array are known to those of skill in the art. Thus, for example, where a colorimetric label is used, simple visualization of the label is sufficient Where a radioactive labeled probe is used, detection of the radiation (e.g. with photographic film or a solid state detector) is sufficient.

In a preferred embodiment, however, the target nucleic acids are labeled with a fluorescent label and the localization of the label on the probe array is accomplished with fluorescent microscopy. The hybridized array is excited with a light source at the excitation wavelength of the particular fluorescent label and the resulting fluorescence at the emission wavelength is detected. In a particularly preferred embodiment, the excitation light source is a laser appropriate for the excitation of the fluorescent label.

The confocal microscope may be automated with a computer-controlled stage to automatically scan the entire high density array. Similarly, the microscope may be equipped with a phototransducer (e.g., a photomultiplier, a solid state array, a CCD camera, etc.) attached to an automated data acquisition system to automatically record the fluorescence signal produced by hybridization to each oligonucleotide probe on the array. Such automated systems are described at length in U.S. Pat. No. 5,143,854, PCT application Ser. No. 20 92/10092, and copending U.S. application Ser. No. 08/195,889 filed on Feb. 10, 1994. Use of laser illumination in conjunction with automated confocal microscopy for signal detection permits detection at a resolution of better than about 100 $\mu$m, more preferably better than about 50 $\mu$m, and most preferably better than about 25 $\mu$m.

One of skill in the art will appreciate that methods for evaluating the hybridization results vary with the nature of the specific probe nucleic acids used as well as the controls provided. In the simplest embodiment, simple quantification of the fluorescence intensity for each probe is determined. This is accomplished simply by measuring probe signal strength at each location (representing a different probe) on the high density array (e.g., where the label is a fluorescent label, detection of the amount of florescence (intensity) produced by a fixed excitation illumination at each location on the array). Comparison of the absolute intensities of an array hybridized to nucleic acids from a "test" sample with intensities produced by a "control" sample provides a measure of the relative expression of the nucleic acids that hybridize to each of the probes.

One of skill in the art, however, will appreciate that hybridization signals will vary in strength with efficiency of hybridization, the amount of label on the sample nucleic acid and the amount of the particular nucleic acid in the sample. Typically nucleic acids present at very low levels (e.g., <1 pM) will show a very weak signal. At some low level of concentration, the signal becomes virtually indistinguishable from background. In evaluating the hybridization data, a threshold intensity value may be selected below which a signal is not counted as being essentially indistinguishable from background.

Where it is desirable to detect nucleic acids expressed at lower levels, a lower threshold is chosen. Conversely, where only high expression levels are to be evaluated a higher threshold level is selected. In a preferred embodiment, a suitable threshold is about 10% above that of the average background signal.

In addition, the provision of appropriate controls permits a more detailed analysis that controls for variations in hybridization conditions, cell health, non-specific binding and the like. Thus, for example, in a preferred embodiment, the hybridization array is provided with normalization controls. These normalization controls are probes complementary to control sequences added in a known concentration to the sample. Where the overall hybridization conditions are poor, the normalization controls will show a smaller signal reflecting reduced hybridization. Conversely, where hybridization conditions are good, the normalization controls will provide a higher signal reflecting the improved hybridization. Normalization of the signal derived from other probes in the array to the normalization controls thus provides a control for variations in hybridization conditions. Typically, normalization is accomplished by dividing the measured signal from the other probes in the array by the average signal produced by the normalization controls. Normalization may also include correction for variations due to sample preparation and amplification. Such normalization may be accomplished by dividing the measured signal by the average signal from the sample preparation/amplification control probes (e.g., the Bio B probes). The resulting values may be multiplied by a constant value to scale the results.

As indicated above, the high density array can include mismatch controls. In a preferred embodiment, there is a mismatch control having a central mismatch for every probe (except the normalization controls) in the array. It is expected that after washing in stringent conditions, where a perfect match would be expected to hybridize to the probe, but not to the mismatch, the signal from the mismatch controls should only reflect non-specific binding or the presence in the sample of a nucleic acid that hybridizes with the mismatch. Where both the probe in question and its corresponding mismatch control both show high signals, or the mismatch shows a higher signal than its corresponding test probe, there is a problem with the hybridization and the signal from those probes is ignored. The difference in hybridization signal intensity between the target specific probe and its corresponding mismatch control is a measure of the discrimination of the target-specific probe. Thus, in a preferred embodiment, the signal of the mismatch probe is subtracted from the signal from its corresponding test probe to provide a measure of the signal due to specific binding of the test probe.

The concentration of a particular sequence can then be determined by measuring the signal intensity of each of the probes that bind specifically to that gene and normalizing to the normalization controls. Where the signal from the probes is greater than the mismatch, the mismatch is subtracted. Where the mismatch intensity is equal to or greater than its corresponding test probe, the signal is ignored. The expression level of a particular gene can then be scored by the number of positive signals (either absolute or above a threshold value), the intensity of the positive signals (either absolute or above a selected threshold value), or a combination of both metrics (e.g., a weighted average).

In some preferred embodiments, a computer system is used to compare the hybridization intensities of the perfect match and mismatch probes of each pair. If the gene is expressed, the hybridization intensity (or affinity) of a perfect match probe of a pair should be recognizably higher than the corresponding mismatch probe. Generally, if the hybridizations intensities of a pair of probes are substantially the same, it may indicate the gene is not expressed. However, the determination is not based on a single pair of probes, the determination of whether a gene is expressed is based on an analysis of many pairs of probes.

After the system compares the hybridization intensity of the perfect match and mismatch probes, the system indicates expression of the gene. As an example, the system may indicate to a user that the gene is either present (expressed), marginal or absent (unexpressed). Specific procedures for data analysis is disclosed in U.S. application Ser. No. 08/772,376, previously incorporated for all purposes.

In addition to high density nucleic acid arrays, other methods are also useful for massive gene expression monitoring. Differential display, described by Liang, P. and Pardee, A. B. (Differential Display of eukaryotic messenger RNA by means of the polymerase chain reaction. *Science* 257:967–971, 1992, incorporated herein by reference for all purposes) provides a useful mean for distinguishing gene expression between two samples. Serial analysis of gene expression, described by Velculescu et al. (Serial Analysis of Gene Expression. Science, 270:484–487, 1995, incorporated herein by reference for all purposes) provides another method for quantative and qualitative analysis of gene expression. Optical fiber oligonucleotide sensors, described by Ferguson et al. (A Fiber-optic DNA biosensor microarray for the analysis of gene expression. Nature-Biotechnology 14:1681–1684, 1996), can also be used for gene expression monitoring.

The following terminology is relevant to the use of gene arrays for determining levels of expression of particular genes.

Massive Parallel Screening: The phrase "massively parallel screening" refers to the simultaneous screening of at least about 100, preferably about 1000, more preferably about 10,000 and most preferably about 1,000,000 different nucleic acid hybridizations.

Mismatch control: The term "mismatch control" or "mismatch probe" refer to a probe whose sequence is deliberately selected not to be perfectly complementary to a particular target sequence. For each mismatch (MM) control in a high-density array there typically exists a corresponding perfect match (PM) probe that is perfectly complementary to the same particular target sequence. The mismatch may comprise one or more bases. While the mismatch(s) may be located anywhere in the mismatch probe, terminal mismatches are less desirable as a terminal mismatch is less likely to prevent hybridization of the target sequence. In a particularly preferred embodiment, the mismatch is located at or near the center of the probe such that the mismatch is most likely to destabilize the duplex with the target sequence under the test hybridization conditions.

mRNA or tanscript: The term "mRNA" refers to transcripts of a gene. Transcripts are RNA including, for example, mature messenger RNA ready for translation, products of various stages of transcript processing. Transcript processing may include splicing, editing and degradation.

Perfect match probe: The term "perfect match probe" refers to a probe that has a sequence that is perfectly complementary to a particular target sequence. The test probe is typically perfectly complementary to a portion (subsequence) of the target sequence. The perfect match (PM) probe can be a "test probe", a "normalization control" probe, an expression level control probe and the like. A perfect match control or perfect match probe is, however, distinguished from a "mismatch control" or "mismatch probe."

Quantifying: The term "quantifying" when used in the context of quantifying transcription levels of a gene can refer to absolute or to relative quantification. Absolute quantification may be accomplished by inclusion of known concentration(s) of one or more target nucleic acids (e.g. control nucleic acids such as Bio B or with known amounts the target nucleic acids themselves) and referencing the hybridization intensity of unknowns with the known target nucleic acids (e.g. through generation of a standard curve). Alternatively, relative quantification can be accomplished by comparison of hybridization signals between two or more genes, or between two or more treatments to quantify the changes in hybridization intensity and, by implication, transcription level.

Up-stream or down-stream gene. If the expression of a first gene is regulated by a second gene, the second gene is called an "up-stream gene" for the first gene and the first gene is the "down-stream" gene of the second gene. The regulation of the first gene by second gene could be through trans-activation. For example, the first gene encodes a transcriptional factor that controls the expression of the second gene. Alternatively, regulation can be by inhibition of transcript degradation. Regulation can also be by inhibition of translation of a transcript. Still other modes of regulation are known in the art and any of these can be used.

It is understood that the examples and embodiments described herein are for illustrative purposes only and that various modifications or changes in light thereof will be suggested to persons skilled in the art and are to be included within the spirit and purview of this application and scope of the appended claims. Many variations of the invention will be apparent to those of skill in the art upon reviewing the above description. By way of example, the invention has been described primarily with reference to the use of a high density oligonuclcotide array, but it will be readily recognized by those of skill in the art that other nucleic acid arrays, other methods of measuring transcript levels and gene expression monitoring at the protein level could be used. The scope of the invention should, therefore, be determined not with reference to the above description, but should instead be determined with reference to the appended claims, along with the full scope of equivalents to which such claims are entitled. All publications, patents, and patent applications cited herein are hereby incorporated by reference for all purposes.

EXAMPLES

Example 1

Ectopic Expression of a Transgene

One application of the present method involves ectopically expressing 50–100 oncogenes and tumor suppressor genes in a "shotgun" approach to identify novel relationships among proteins. Many of the genes that have been causally linked to cancer development will likely cluster in a limited number of key cellular pathways. Several examples exist in which genes mutated in disparate contexts turn out to play roles in common pathways. Perhaps the most striking case involves a signaling network that regulates the cell cycle. At least seven components of this network (ATM, p53, MDM2, p16, cdk4, cyclin D1, and RB) exhibit frequent alterations in various cancers, indicating the critical role that disruption of this pathway plays in tumor formation.

One model system involves the ATM, p53, and p21 proteins. These three proteins act in a DNA damage-response growth regulatory axis in which ATM stimulates p53 activity, and p53 transcriptionally activates p21. However, the exact biochemical relationships among these molecules and as-yet unidentified pathway members remains unclear. Primary embryonic fibroblasts from wild-type mice, as well as from mice individually null for ATM, p53, and p21 can be used. Cells of each genotype can be gamma-irradiated in order to activate the DNA damage-response pathway, and expression profiles can be generated from irradiated (at 1 and 4 hours post-irradiation) and non-irradiated cells.

Two other model systems involve ectopic expression of transgenes in cultured cell lines. U2OS osteosarcoma cells stably transfected with tetracycline-repressible WT1 (Wilm's Tumor susceptibility gene) or BRCA1 (Breast cancer susceptibility gene) expression constructs can also be used. In this so-called "tet-off" induction system, the recombinant gene is induced by withdrawal of tetracycline from the tissue culture medium. Upon induction of WT1 and BRCA1 expression, we identified 18 and 16 endogenous genes, respectively (of 7000 genes monitored), that displayed reproducible expression changes of 3-fold or greater. None of the candidate functional mediators (CFMs) identified in the WT1 expression screen overlapped with those identified in the BRCA1 screen, indicating that these expression changes were not artifactually linked to the induction system or host cell type employed in the screening. Literature searches indicated that roughly half of the CFMs identified in each study had either correlative or causative links to tumorigenesis, and several have been proposed, or are in clinical use, as prognostic or diagnostic markers. These findings support the physiological relevance of expression changes identified in cell culture-based recombinant expression systems. Putative mechanistic advantages of BRCA1 inactivation in tumors can be inferred from the identity of its CFMs (FIG. 1), but detailed pathway modeling requires additional expression profiling experiments.

An iterative expression profiling strategy can be used in which CFMs identified in an initial screen are themselves recombinantly expressed in subsequent screens. For example, using the tet-off induction system, we can ectopically express one WT1 CFM (amphiregulin) and one BRCA1 CFM (GADD45) following stable transfection in U2OS cells. Amphiregulin and GADD45 transfectants can be profiled pre- and post-induction. The resultant expression changes constitute a subset of those observed following BRCA1 and WT1 induction.

Amphiregulin and GADD45 have been expressed in U2OS cells in transient transfection experiments, and the resulting phenotype (reduced colony formation, in both cases) was identical to that obtained following transient transfection of either BRCA1 or WT1 in these same cells. Furthermore, in in situ hybridization experiments WT1 and amphiregulin co-localized to developing human glomeruli during identical stages of embryogenesis. Thus amphiregulin and GADD45 are implicated as transducers of WT1 and BRCA1 tumor suppressive function. Other data are consistent with this finding. For example, treatment of several human carcinoma cell lines with soluble amphiregulin (a member of the EGF family) results in growth inhibition. The BRCA1 and GADD45 proteins have been correlatively linked to DNA damage response. BRCA1 binds to Rad51, a homolog of bacterial recA involved in DNA repair following exposure to ionizing radiation. Moreover, treatment of cell lines with ionizing radiation induces alterations in BRCA1 phosphorylation and subnuclear localization, as well as GADD45 transcription. Lastly, GADD45 binds PCNA, a component of DNA replication and repair complexes, and enhances nucleotide excision repair in vitro. Together, the above data suggest that GADD45 functions downstream of BRCA1, and that amphiregulin functions downstream of WT1.

The amphiregulin and GADD45 expression constructs can be produced using PCR and standard cloning methods. The inserts can be screened using custom polymorphism-detection arrays or by standard gel-based sequencing methods to ensure that no mutations were introduced during PCR amplification. Expression vectors can be stably transfected into U2OS cells, and clones expressing high levels of the recombinant genes can be identified by hybridization of RNA from those cell lines to these same polymorphism-detection arrays (using different software, polymorphism-detection arrays can also be used for expression monitoring). Following subsequent preparative-scale inductions, RNA can be isolated, biotin-labeled, and hybridized to oligonucleotide arrays. The chips can then be washed, treated with streptavidin-coupled phycoerythrin (to link a fluorophore to the biotinylated RNA), and scanned with a laser confocal fluorescence microscope. Fluorescence intensities can be used to calculate absolute mRNA abundances, as well as expression differences from sample to sample. RNA derived from the ATM-null, p53-null, p21-null, and wildtype murine cells can be treated in the same fashion.

Example 2

Hybridization-based Assay for Generating Expression Profiles

Messenger RNA levels are determined by hybridization of complete mRNA populations to sets of arrays containing hundreds of thousands of chemically synthesized oligonucleotides. The oligonucleotides are synthesized in situ on glass supports using light-directed, solid-phase combinatorial chemistry. Because the arrays are designed and synthesized based on sequence information alone, they provide a direct link between genomic sequence and measurements of differential gene expression. Each synthesis feature consists of more than $10^7$ copies of a particular oligonucleotide.

For each mRNA sample, the expression levels of thousands of full-length human genes can be monitored. For each gene, up to 20 complementary oligomers are chosen based on automated selection criteria The criteria include tests for sequence uniqueness relative to the rest of the genome and the absence of sequence features (e.g., self-complementarity or clusters of single nucleotides) that have been determined to adversely affect hybridization behavior on arrays. The use of sets of oligonucleotides for each gene provides redundancy in the detection and analysis of the data, mitigates the potentially confounding effects of occasional cross-hybridization, and makes it so all oligonucleotides do not have to hybridize identically in order to obtain quantitative information. To further increase the sensitivity and specificity of detection, each complementary oligonucleotide (perfect match, or PM) is synthesized with a closely related mismatch (MM) partner in a physically adjacent position. The mismatch partner is identical except for a single base difference at the central position of the oligomer. The MM oligonucleotide of each pair serves as an internal control that allows consistent hybridization patterns (patterns of PM signals that are larger than the corresponding MM signals) to be recognized. Quantitative image analysis is based on the average of the differences between the PM and MM partners, so that nonspecific and background contributions tend to cancel, while specific hybridization signals tend to add constructively across the set of oligonucleotide pairs for each gene. These hybridization signals are quantitative over three orders of magnitude, from 1:300,000 to 1:300.

Example 3

Computational Modeling

Computational models can be tailored to the analysis of simple experimental systems. They lend themselves well to visual representation of signaling networks. They provide a convenient mechanism to facilitate communication between biologists and computer scientists.

We have chosen a set of reductionist experimental systems that can yield data about the connectivity of these networks. Given connectivity data for such networks, very simple combinatorial models allow us to deduce significant properties of these networks. Such reverse-engineering procedures require that the experimental data on which they are based can produce reliable connectivity information.

Figure 2:
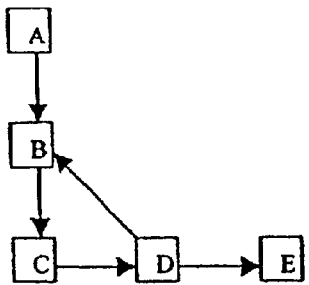
FIGS. 2a through 2f show that edges transmit changed expression levels with high reliability. Many graphs are compatible with the data, but all such graphs are subgraphs of the transitive closure graph G*.
Figure 2:
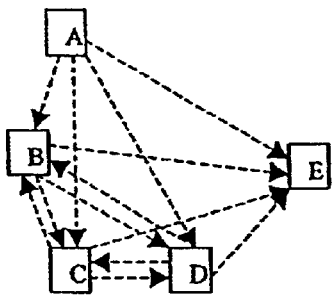
Figure 2:
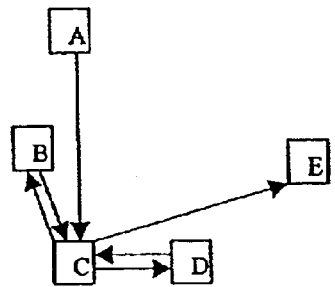
Figure 2:
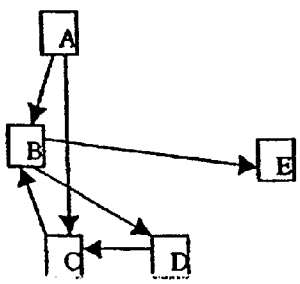
Figure 2:
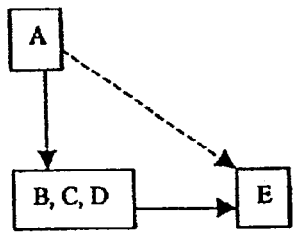
Figure 3:
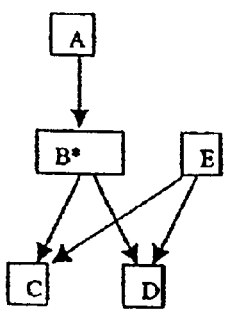
FIGS. 3a through 3c demonstrate that interactions not at the level of expression are concealed in the connectivity graph. Genes B* (regulated by A), E (not regulated by A), and A are indistinguishable at the expression level.
Figure 3:
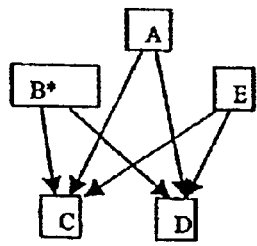

The systems described in the previous sections display the common feature of an initiating genetic alteration resulting in expression effects on other genes. We have devised a simple model (exemplified in FIG. 2) that examines the connectivity of a signaling network. We can examine this model, first in an idealized case, and then adding more details obtained from experimentation. In our model, the network is represented using a "graph," genes correspond to "nodes," and directional signals between pairs of genes correspond to "edges." The true graph reflects the actual relationships among the nodes (example in FIG. 2a). Either a gene, A, affects another gene, B, directly (the edge exists), and transmits change, or gene B is not directly affected by gene A, in which case the edge does not exist. Note that "direct" in this case means without involvement of other intermediary genes.

In contrast to most other models, we represent the experimentally observed states of genes in a relative sense as "changed" or "unchanged", rather than in an absolute sense as "expressed" or "unexpressed", since we are interested in the flow of signals along pathways. In this model, the genes in our graph possess only two states, "0", standing for "unchanged with respect to a control", and "1", standing for "significantly changed with respect to a control." Data from an experiment is reduced to a collection of genes, each either in state 0 or 1. Experimental induction or deletion of a gene, A, can then produce expression changes in a set of genes (Example 2b). The genes in this set are exactly those genes that have paths leading to them from A (those nodes connected, directly or indirectly, to node A in the true graph). Furthermore, if genes have paths leading to them from gene A, then there is a path leading from A to every gene connected to A. In this case, the set of genes associated with induction of gene B is a subset of the genes associated with induction of gene A, and gene B has a path leading to it from gene A.

In our two ectopic expression systems, we have already determined the set of expression alterations associated with WT1 and BRCA1 induction. We can generate expression profiles following amphiregulin and GADD45 induction and assess whether the affected genes are a subset of those altered by WT1 and BRCA1 induction, respectively. Conversely, in the gene knockout model, we expect to observe expression subsets reflecting the absence of altered expression following DNA damage (as compared to the response of wildtype cells to DNA damage). For example, deletion of p53 should result in failure to produce expression changes in a set of genes; the affected genes should be a subset of those that fail to change in expression following DNA damage in ATM-null cells.

There are some combinatorial relationships that may not be captured by gene-induction systems or gene-deletion systems alone. For example, if upregulation of gene A and gene B is necessary to induce gene C, then a change in gene A alone can not necessarily affect gene C. These relationships could however be assessed using a system in which the expression of genes A and B can be individually suppressed (as in a gene knockout). In this case, down-regulation of either gene A or gene B (assuming that they are expressed at the beginning of the experiment) can affect gene C. Mathematically, we can easily capture "or" relationships, but not "and" relationships. However, as we just described, we can always represent an "and" relationship as an "or" relationship: A and B=not ((not A) or (not B)). Thus, combining experimental systems to enable both up-regulation and down-regulation is necessary to assess such relationships.

In an ideal case, we obtain connectivity information for each gene. In this case we can obtain an exact representation of the transitive closure of the true graph. This transitive closure is that graph in which, for any two nodes A and B, there is an edge from A to B if and only if there is a path from A to B in the graph G (Example 2c). The connectivity data table in this case is exactly the adjacency matrix for the transitive closure graph. There is an edge A→B between two genes A and B in the transitive closure graph if gene B resides in state 1 in an experiment in which gene A is placed in state 1. Note that there may be many possible graphs having the same transitive closure, and hence experiments of this type cannot distinguish the true graph from other graphs consistent with the data (FIGS. 2d and 2e).

A useful minimal structure for analytical purposes is the "condensed graph." Any transitive closure graph decomposes into two types of components: strongly connected components (SCCs), in which every node is connected to every other, and a directed acyclic component connecting the SCCs. A condensed graph is produced by reducing each SCC to a corresponding "super" node. This procedure leaves a directed, acyclic graph between such nodes. Edges in this acyclic graph may be required by the experimental data, or redundant, and it is useful to mark them one way or another.

There are several well-known algorithms for producing instances of minimal graphs having the same transitive closure as a given graph. These algorithms are, in general, computationally infeasible for large graphs, but are feasible for the transitive closure graphs discussed here. Every strongly connected component may be represented as a cycle on its nodes, allowing redundant edges to be removed from the remaining graph, leaving a minimal structure summarizing the properties of the graph. Such a minimal structure may be a useful visualization tool in summarizing the data set, although it may not resemble the true graph. Due to this lack of resemblance, we can not invoke such models.

This simple model of connectivity allows us to map the major features of gene regulatory pathways. Even in the most ideal case, obtaining the exact signaling network is infeasible, although much information about the properties of the network can be obtained. Representing the network as a graph allows us to exploit standard combinatorial algorithms. See for example, Martello (1982), Khuller (1995), and van Leeuwen (1990), each of which is expressly incorporated herein.

The above disclosure generally describes the present invention. A more complete understanding can be obtained by reference to the following specific examples which are provided herein for purposes of illustration only, and are not intended to limit the scope of the invention.

References Cited

Akutsu, T., Kuhara, S., Maruyama, O., and Miyano, S. (1998). "Identification of gene regulatory networks by strategic gene disruptions and gene overexpression." *Proceedings of the Ninth Annual ACM-SIAM Symposium on Discrete Algorithms*, 695–702.

Chee, M., Yang, R, Hubbell, E., Bemo, A., Huang, X. C., Stern, D., Winkler; J., Lochart, D. J., Morris, M. S., and Fodor, S. P. (1996). "Accessing genetic information with high-density DNA arrays." *Science*, 274(5287), 610–4.

Deng, C., Zhang, P., Harper, J. W., Elledge, S. J., and Leder, P. (1995). "Mice lacking p21CIP1/WAF1 undergo normal development, but are defective in G1 checkpoint control." *Cell*, 82(4), 675–84.

Donehower, L. A., Harvey, M., Slagle, B. L., McArthur, M. J., Montgomery, C. A., Jr., Butel, J. S., and Bradley, A. (1992). "Mice deficient for p53 are developmentally normal but susceptible to spontaneous tumours." *Nature*, 356(6366), 215–21.

Elson, A., Wang, Y., Daugherty, C. J., Morton, C. C., Zhou, F., Campos-Torres, J., and Leder, P. (1996). "Pleiotropic defects in ataxia-telangiectasia protein-deficient mice." *Proc Natl Acad Sci USA*, 93(23), 13084–9.

Fodor, S. P., Read, J. L., Pirrung, M. C., Stryer, L., Lu, A. T., and Solas, D. (1991). "Light-directed, spatially addressable parallel chemical synthesis." *Science*, 251 (4995), 767–73.

Gossen, M., and Bujard, H. (1992). "Tight control of gene expression in mammalian cells by tetracycline-responsive promoter." *Proc Natl Acad Sci USA*, 89(12), 5547–51.

Khuller, S., Raghavachari, B., and Young, N. (1995). "Approximating the minimum equivalent digraph." *SIAM J Comp*, 24(4), 859–872.

Liang, S., Fuhrman, S., and Somogyi, R. (1998). "REVEAL, a general reverse engineering algorithm for inference of genetic network architectures." *Pacific Symposium on Biocomputing*, 3, 18–29.

Lockhard, D. J., Dong, H., Byrne, M. C., Follettie, M. T., Gallo, M. V., Chee, M. S., Mittann, M., Wang, C., Kobayashi, M., Horton, H., and Brown, E. L. (1996). "Expression monitoring by hybridization to high-density oligonucleotide arrays." *Nat Biotechnol*, 14(13), 1675–80.

Martello, S., and Toth, P. (1982). "Finding a minimum equivalent graph of a diagraph." *Networks*, 12, 89–100.

Morgan, S. E., and Kastan, M. B. (1997). "p53 and ATM: cell cycle, cell death, and cancer." *Adv Cancer Res*, 71, 1–25.

Morin, P. J., Sparks, A. B., Koriiinek, V., Barker, N., Clevers, H., Vogelstein, B., and Kinzler, K. W. (1997). "Activation of beta-catenin-Tcf signaling in colon cancer by mutations in beta-catenin or APC" *Science*, 275(5307), 1787–90.

Papathanasiou, M. A., Kerr, N. C., Robbins, J. H., McBride, O. W., Alamo, I., Jr., Barrett, S. F., Hickson, I. D., and Fornace, A. J., Jr. (1991). "Induction by ionizing radiation of the gadd45 gene in cultured human cells: lack of mediation by protein kinase C." *Mol Cell Biol*, 11(2), 1009–16.

Pease, A. C., Solas, D., Sullivan, E. J., Cronin, M. T., Holmes, C. P., and Fodor, S. P. (1994). "Light-generated oligonucleotide arrays for rapid DNA sequence analysis." *Proc Natl Acad Sci USA*, 91(11), 5022–6.

Plowman, G. D., Green, J. M., McDonald, V. L., Neubauer, M. G., Disteche, C. M., Todaro, G. J., and Shoyab, M. (1990). "The amphiregulin gene encodes a novel epidermal growth factor-related protein with tumor-inhibitory activity." *Mol Cell Biol*, 10(5), 1969–81.

Rubinfeld, B., Robbins, P., El-Gamil, M., Albert, I., Porfiri, E., and Polakis, P. (1997). "Stabilization of beta-catenin by genetic defects in melanoma cell lines." *Science*, 275(5307), 1790–2.

Scully, R., Chen, J., Ochs, R. L., Keegan, K., Hoekstra, M., Feunteun, J., and Livingston, D. M. (1997a). "Dynamic changes of BRCA1 subnuclear location and phosphorylation state are initiated by DNA damage." *Cell*, 90(3), 425–35.

Scully, R., Chen, J., Plug, A., Xiao, Y., Weaver, D., Feunteun, J., Ashley, T., and Livingston, D. M. (1997b). "Association of BRCA1 with Rad51 in mitotic and meiotic cells." *Cell*, 88(2), 265–75.

Sherr, C. J. (1996). "Cancer cell cycles." *Science*, 274 (5293), 1672–7.

Shoyab, M., McDonald, V. L., Bradley, J. G., and Todaro, G. J. (1988). "Amphiregulin: a bifunctional growth-modulating glycoprotei produced by the phorbol 12-myristate 13-acetate-treated human breast adenocarcinoma cell line MCF-7." *Proc Natl Acad Sci USA*, 85(17), 6528–32.

Smith, M. L., Chen, I. T., Zhan, Q., Bae, I., Chen, C. Y., Gilmer, T. M., Kastan, M. B., O'Connor, P. M., and Fomace, A. J., Jr. (1994). "Interaction of the p53-regulated protein Gadd45 with proliferating cell nuclear antigen." *Science*, 266(5189), 1376–80.

Sparks, A. B., Morin, P. J., Vogelstein, B., and Kinzler, K. W. (1998). "Mutational analysis of the APC/beta-catenin/Tcf pathway in colorectal cancer." *Cancer Res*, 58(6), 1130–4.

Thomas, J. E., Smith, M., Tonkinson, J. L., Rubinfeld, B., and Polakis, P. (1997). "Induction of phosphorylation on BRCA1 during the cell cycle and after DNA damage." *Cell Growth Differ*, 8(7), 801–9.

van Leeuwen, J. (1990). "Graph Algorithms." *Handbook of Theoretical Computer Science*, North Holland, Amsterdam, 525–631.

Wodicka, L., Dong, H., Mittmann, M., Ho, M. H., and Lockhard, D. J. (1997). "Genome-wide expression monitoring in Saccharomyces cerevisiae." *Nat Biotechnol*, 15(13), 1359–67.

What is claimed is:

1. A method of determining candidate functional mediators of a selected gene, comprising the steps of:

a. altering expression of a first selected gene in a first of two populations of identical cells;

b. comparing expression levels of a first set of genes in the two populations of cells, wherein the expression levels are measured on oligonucleotide arrays;

c. identifying genes in the first set whose expression levels differ between the two populations of cells, wherein the genes identified are candidate functional mediators of the selected gene;

d. altering expression of a second selected gene in one of a third and fourth populations of cells, wherein the third and fourth populations comprise identical cells, wherein the second selected gene is a candidate functional mediator of the first selected gene;

e. comparing expression levels of a second set of genes in the third and fourth populations of cells, wherein the expression levels are measured on oligonucleotide arrays;

f. identifying genes in the second set whose expression levels differ between the third and fourth populations of cells, wherein the genes identified are candidate functional mediators of the second selected gene.

2. The method of claim 1 wherein the step of altering (a) comprises adding an exogenous regulatory agent to the first population of cells, wherein the regulatory agent alters expression of the first selected gene.

3. The method of claim 1 wherein the step of altering (d) comprises adding an exogenous regulatory agent to the third populations of cells, wherein the regulatory agent alters expression of the second selected gene.

4. The method of claim 1 wherein the step of altering (a) comprises mutagenizing the first selected gene.

5. The method of claim 1 wherein the step of altering (d) comprises mutagenizing the second selected gene.

6. The method of claim 1 wherein the step of altering (a) comprises administering an antisense construct to the first population, wherein the antisense construct encodes an RNA which is complementary to mRNA transcribed from the first selected gene.

7. The method of claim 1 wherein the step of altering (d) comprises administering an antisense construct to the third population, wherein the antisense construct encodes an RNA which is complementary to mRNA transcribed from the second selected gene.

8. The method of claim 1 wherein the step of altering (a) comprises administering a ribozyme construct to the first population, wherein the ribozyme construct encodes an RNA which cleaves mRNA transcribed from the first selected gene.

9. The method of claim 1 wherein the step of altering (d) comprises administering a ribozyme construct to the third population, wherein the ribozyme construct encodes an RNA which cleaves mRNA transcribed from the second selected gene.

10. The method of claim 1 wherein the step of altering (a) comprises altering copy number of the first selected gene in the first population of cells.

11. The method of claim 1 wherein the step of altering (d) comprises altering copy number of the second selected gene in the third population of cells.

12. The method of claim 1 wherein steps (d–f) are repeated with a plurality of candidate functional mediators identified in step (c).

13. The method of claim 1 wherein steps (a–c) are repeated using a candidate functional mediator of the second selected gene as a first selected gene.

14. The method of claim 1 wherein steps (a–f) are repeated using a candidate functional mediator of the second selected gene as a first selected gene.

15. The method of claim 1 wherein the first and second selected genes are tumor suppressor genes.

16. The method of claim 1 wherein the first and second selected genes are oncogenes.

17. A method of identifying pathways of functional mediators of a selected gene, comprising the steps of:

a. altering expression of a first selected gene in a first of two populations of identical cells;

b. comparing expression levels of a first set of genes in the two populations of cells, wherein the expression levels are measured on oligonucleotide arrays;

c. identifying genes in the first set whose expression levels differ between the two populations of cells, wherein the genes identified form a set of candidate functional mediators of the first selected gene;

d. altering expression of a second selected gene in one of a third and fourth populations of cells, wherein the third and fourth populations comprise identical cells;

e. comparing expression levels of a second set of genes in the third and fourth populations of cells, wherein the expression levels are measured on oligonucleotide arrays;

f. identifying genes in the second set whose expression levels differ between the third and fourth populations of cells, wherein the genes identified form a set of candidate functional mediators of the second selected gene;

g. comparing the candidate functional mediators identified of the first and second selected genes, wherein genes which are identified as candidate functional mediators of both selected genes suggest that the first and second selected genes are components of a common pathway, wherein failure to identify a candidate functional mediator of both selected genes suggests that the two selected genes are in different pathways, wherein identification of a set of candidate functional mediators of the first selected gene as a subset of the set of candidate functional mediators of the second selected gene suggests that the first selected gene is downstream in a pathway relative to the second selected gene, and wherein a candidate functional mediator which is identified in only one of the two sets of candidate functional mediators is identified as upstream in the pathway of a selected gene from a point of convergence with the pathway of the other selected gene, if the sets of candidate functional mediator genes of the first and second selected genes contain common members.

18. The method of claim 17 wherein the step of altering (a) comprises adding an exogenous regulatory agent to the first population of cells, wherein the regulatory agent alters expression of the first selected gene.

19. The method of claim 17 wherein the step of altering (d) comprises adding an exogenous regulatory agent to the third populations of cells, wherein the regulatory agent alters expression of the second selected gene.

20. The method of claim 17 wherein the step of altering (a) comprises mutagenizing the first selected gene.

21. The method of claim 17 wherein the step of altering (d) comprises mutagenizing the second selected gene.

22. The method of claim 17 wherein the step of altering (a) comprises administering an antisense construct to the first population, wherein the antisense construct encodes an RNA which is complementary to mRNA transcribed from the first selected gene.

23. The method of claim 17 wherein the step of altering (d) comprises administering an antisense construct to the third population, wherein the antisense construct encodes an RNA which is complementary to mRNA transcribed from the second selected gene.

24. The method of claim 17 wherein the step of altering (a) comprises administering a ribozyme construct to the first population, wherein the ribozyme construct encodes an RNA which cleaves mRNA transcribed from the first selected gene.

25. The method of claim 17 wherein the step of altering (d) comprises administering a ribozyme construct to the third population, wherein the ribozyme construct encodes an RNA which cleaves mRNA transcribed from the second selected gene.

26. The method of claim 17 wherein the step of altering (a) comprises altering copy number of the first selected gene in the first population of cells.

27. The method of claim 17 wherein the step of altering (d) comprises altering copy number of the second selected gene in the third population of cells.

28. The method of claim 17 wherein the first and second selected genes are tumor suppressor genes.

29. The method of claim 17 wherein the first and second selected genes are oncogenes.

30. A method to determine a pathway of gene products, comprising the step of:

comparing a first set of candidate functional mediator genes identified by the process of:
(a) comparing expression levels of a set of genes in two populations of identical cells, wherein a first of the two populations of cells has been treated to alter expression of a first selected gene, wherein the expression levels are measured on oligonucleotide arrays;
(b) identifying genes in the set of genes whose expression levels differ between the two populations of cells, wherein the genes identified are candidate functional mediators of the first selected gene;

with a second set of candidate functional mediator genes identified by the process of:
(c) comparing expression levels of the set of genes in a third and fourth population of cells, wherein the third population of cells has been treated to alter expression of a second selected gene, wherein the expression levels are measured on oligonucleotide arrays;
(d) identifying genes in the set of genes whose expression levels differ between the third and fourth populations of identical cells, wherein the genes identified are candidate functional mediators of the second selected gene;

identifying the first and second selected genes as components of a common pathway when one or more genes are found to be candidate functional mediators of both of said first and said second selected genes.

31. A method to determine a pathway of gene products, comprising the step of:

comparing a first set of candidate functional mediator genes identified by the process of:
(a) comparing expression levels of a set of genes in two populations of identical cells, wherein a first of the two populations of cells has been treated to alter expression of a first selected gene, wherein the expression levels are measured on oligonucleotide arrays;
(b) identifying genes in the set of genes whose expression levels differ between the two populations of cells, wherein the genes identified are candidate functional mediators of the first selected gene;

with a second set of candidate functional mediator genes identified by the process of:
(c) comparing expression levels of the set of genes in a third and fourth population of cells, wherein the third population of cells has been treated to alter expression of a second selected gene, wherein the expression levels are measured on oligonucleotide arrays;
(d) identifying genes in the set of genes whose expression levels differ between the third and fourth populations of identical cells, wherein the genes identified are candidate functional mediators of the second selected gene;

identifying the first and second selected genes as being in different pathways when no gene is identified as being a candidate functional mediator of both of said first and said second selected genes.

32. A method to determine a pathway of gene products, comprising the step of:

comparing a first set of candidate functional mediator genes identified by the process of:
(a) comparing expression levels of a set of genes in two populations of identical cells, wherein a first of the two populations of cells has been treated to alter expression of a first selected gene, wherein the expression levels are measured on oligonucleotide arrays;
(b) identifying genes in the set of genes whose expression levels differ between the two populations of cells, wherein the genes identified are candidate functional mediators of the first selected gene;

with a second set of candidate functional mediator genes identified by the process of:
(c) comparing expression levels of the set of genes in a third and fourth population of identical cells, wherein the third population of cells has been treated to alter expression of a second selected gene, wherein the expression levels are measured on oligonucleotide arrays;
(d) identifying genes in the set of genes whose expression levels differ between the third and fourth populations of cells, wherein the genes identified are candidate functional mediators of the second selected gene;

identifying a gene which is identified as a candidate functional mediator of only one of said first and said second selected genes as upstream in the pathway of the first or second selected gene from a point of convergence with the pathway of the second or first selected gene, if the first and second sets of candidate functional mediator genes contain common members.

33. A method to determine a pathway of gene products, comprising the step of:

comparing a first set of candidate functional mediator genes identified by the process of:
(a) comparing expression levels of a set of genes in two populations of identical cells, wherein a first of the two populations of cells has been treated to alter expression of a first selected gene, wherein the expression levels are measured on oligonucleotide arrays;
(b) identifying genes in the set whose expression levels differ between the two populations of cells, wherein the genes identified are candidate functional mediators of the first selected gene;

with a second set of candidate functional mediator genes identified by the process of:
(c) comparing expression levels of the set of genes in a third and fourth population of identical cells, wherein the third population of cells has been treated to alter expression of a second selected gene, wherein the expression levels are measured on oligonucleotide arrays;
(d) identifying genes whose expression levels differ between the third and fourth populations of cells, wherein the genes identified are candidate functional mediators of the second selected gene;

identifying the first selected gene as downstream in a pathway relative to the second selected gene if the set of candidate functional mediators of the first selected gene is a subset of the set of candidate functional mediators of the second selected gene.

* * * * *